United States Patent [19]

Spiegelman et al.

[11] Patent Number: 5,306,729
[45] Date of Patent: Apr. 26, 1994

[54] METHOD FOR EFFECTING VASODILATION WITH MONOGLYCERIDES

[75] Inventors: Bruce M. Spiegelman, Waban; William O. Wilkison, Boston; Sven Bursell, Newton, all of Mass.

[73] Assignees: Joslin Diabetes Center; Dana-Farber Cancer Institute, both of Boston, Mass.

[21] Appl. No.: 840,909

[22] Filed: Feb. 25, 1992

[51] Int. Cl.⁵ ............... A61K 31/22; A61K 31/23
[52] U.S. Cl. .................... 514/546; 514/549; 514/552; 514/912
[58] Field of Search ........... 514/546, 549, 552, 912

[56] References Cited

PUBLICATIONS

Dobson et al., "1-Butyryl-Glycerol: A Novel Angiogenesis Factor Secreted by Differentiating Adipocytes", Cell, 61:223–230 (Apr. 20, 1990).
Wilkinson et al., "Biosynthetic Regulation of Monobutyrin, an Adipocyte-secreted Lipid with Angiogenic Activity", Journal Biol. Chem., 266:16886–16891 (Sep. 5, 1991).
Birkhahn et al., "Intravenous feeding of the rat with short chain fatty acid esters", The American Journal of Clinical Nurtrition, 30:2078–2082 (Dec. 1977).
White et al., "Identification of Capric Acid as a Potent Vasorelaxant of Human Basilar Arteries", Stroke, 22:469–476 (Apr. 1991).
White et al., "Capric Acid As A Potent Dilator Of Canine Vessels In Vitro and In Vivo", Gen. Pharmac., 22:741–748 (1991).
Prewitt et al., "Antihypertensive Polar Renomedullary Lipid, A Semisynthetic Vasodilator", Hypertension, 1:299–308 (May–Jun. 1979).
Muirhead et al., "Cardiovascular effects of antihypertensive renomedullary lipids (APRL and ANRL)", Acta Physiol. Scand., 117:465–467 (1983).
Muirhead et al., "Cardiovascular Effects of Antihypertensive Polar and Neutral Renomedullary Lipids", Hypertension, Supp. I, 5:I-112–118 (Mar.–Apr. 1983).
Faber et al., "Regional Hemodynamic Effects of Antihyper-tensive Renomedullary Lipids in Conscious Rats", Hypertension, 6:495–501 (Jul.–Aug. 1984).
Muirhead et al., "The Antihypertensive Function of the Kidney; Its Elucidation by Captopril plus Unclipping", Hypertension, Supp. I, 7:I-127–135 (May–Jun. 1985).
Muirhead et al., "Biologic Contrasts Between Medullipin I and Vasoactive Glyceryl Compounds", Amer. Jour. Med. Sci., 298:93–103 (Aug. 1989).
Muirhead et al., "Secretion Of Medullipin I By Isolated Kidneys Perfused Under Elevated Pressure", Clinical and Experimental Pharmacology and Physiology, 18:409–417 (1991).
Muirhead et al., "Antihypertensive Action of Medullipin I Given by Mouth", Hypertension, 17:1092–1096 (Jun. 1991).
Okumura et al., "Effect Of Monoglycerides On The Percutaneous Absorption Of Papaverine Hydrochloride", Drug Design and Delivery, 6:137–148 (1990).

Primary Examiner—Zohreh A. Fay
Attorney, Agent, or Firm—Julia D. Hart

[57] ABSTRACT

The invention provides a novel method of effecting vasodilation in a warm-blooded animal in need of such treatment and involves administering to a warm-blooded animal an effective amount of a vasodilatory monoglyceride of the formula:

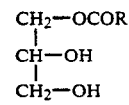

wherein R is a straight or branched chain aliphatic hydrocarbyl substituent of 2–7 carbon atoms, preferably 3–5 carbon atoms, which is saturated or unsaturated, and which is substituted or unsubstituted with one or more substituents that do not interfere with vasodilatory activity.

6 Claims, 4 Drawing Sheets

METHOD FOR EFFECTING VASODILATION WITH MONOGLYCERIDES

GOVERNMENT RIGHTS IN INVENTION

This invention was made with the support of Government Grants 5R01DK42420-9 and 5F32DK08277-03 from the National Institutes of Health and U.S. Army Grant DAMD 17-91-2-1010. The government of the United States of America has certain rights in this invention.

TECHNICAL FIELD OF THE INVENTION

The invention relates to effecting vasodilation. More particularly, it relates to the use of short and medium chain monoglycerides effective in stimulating vasodilation in warm-blooded animals.

BACKGROUND OF THE INVENTION

Glycerides are fatty acid esters of glycerol. Those in which all three of the glycerol hydroxyl groups are esterified are called triglycerides. Such compounds account for most of the substance of vegetable and animal fats. When only one or two of the hydroxyl groups are esterified with fatty acid, the resulting glycerides are called monoglycerides and diglycerides, respectively. Mono- and diglycerides occur in only a small quantity in the fats synthesized in nature, but are the intermediate products of the hydrolysis of fats. Both long and short chain mono- and diglycerides are known mainly as laboratory products prepared for research or as products manufactured for man's use. Richardson, A. S., "Glycerides," *The Encyclopedia of Chemistry*, (Hampel and Hawley eds. 1973).

There have been few reports concerning the biological activity of monoglycerides, although isolated references to biological activities of such compounds do exist. For example, Birkhahn et al., demonstrated the possibility of using butyric acid, in the water soluble form of monobutyrin, as a source of intravenous nutrition by infusing the monoglyceride into rats. *The American Journal of Clinical Nutrition*, 2078-2082 (December 1977). This study showed that the animals could tolerate very high infusions of monobutyrin, up to 27 gm/kg a day, with little or no resulting toxicity and that the compound could provide calories for the animals when infused intravenously.

Another group experimentally demonstrated that monoglycerides having C5-C12 alkyl side chains, especially glyceryl monocaprylate, can be used to enhance the permeability of skin to certain water soluble chemicals and drugs. Okumura et al., *Drug Design and Delivery*, 6:137-148 (1990).

In 1990, Dobson et al described 1-butyryl-glycerol (monobutyrin) as a novel angiogenic compound that is synthesized naturally and secreted during the differentiation of 3T3-F442A preadipocytes into adipocytes. Angiogenesis refers to the growth of new blood vessels and involves the growth of capillaries composed of endothelial cells. Monobutyrin was shown to promote angiogenesis in the chick chorioallantic membrane assay and motility of isolated endothelial cells in vitro. These results, coupled with an observed 200-fold increase in monobutyrin levels during the adipose differentiation process, suggested that monobutyrin is an important regulatory factor in the development of adipose tissue vasculature. *Cell*, 61: 223-230, (Apr. 20, 1990).

The discovery of monobutyrin as a naturally occurring angiogenic factor resulted in the filing of a patent application, U.S. Ser. No. 07/327,314, directed to the use of monobutyrin and other short chain monoglycerides of the formula $CH_2OHCHOHCH_2OCOR$, wherein R is a straight or branched chain hydrocarbyl having 2-10 carbon atoms, saturated or unsaturated, in stimulating angiogenesis, especially for wound healing.

In later work by this group, which includes several of the inventors herein, it was shown that monobutyrin production increases substantially at the onset of lipolysis and that monobutyrin production is surprisingly cell specific. Conditioned medium from several other cell lines representative of actively metabolizing tissue failed to reveal detectable levels of monobutyrin. This cell specificity, coupled with knowledge of other bioeffecting molecules having multiple functions in vivo, led the group to consider that monobutyrin might be a pleiotropic effector having multiple functions in blood vessel biology. Because vessels in adipose tissue are known to vasodilate during lipolysis, a correlative hypothesis was made that monobutyrin could be involved in vasodilation and/or vascular permeability. Wilkison et al, *The Journal of Biological Chemistry*, 25:16886-16891 (September, 1991). The hypothesis was not supported by experimentally, and indeed, was nothing more than conjecture at the time. It is well known from the literature that the concentration of other factors such as glycerol, which do not have vasodilatory activity, also increases after the onset of lipolysis, making it more likely than not that the hypothesized correlation would not be substantiated. It is believed that short chain monoglycerides have not otherwise been associated with vasodilatory activity There is at least one report in the literature of a long chain monoglyceride, monoolein (C18:1), having a depressor effect on blood pressure. Muirhead et al., *The American Journal Of The Medical Sciences*, 298:2 93-103 (August 1989). The vasodilatory capability of monoolein was reported to be dependent upon hepatic activation, as evidenced by a period of latency between intravenous infusion of the compound and observation of the depressor effect of the compound and a loss of activity upon removal of the liver. In addition, free fatty acids, particularly caprate, a C10 fatty acid, have been associated with vasodilatory activity. White et al., *Stroke*, 22:4, 469-476 (April 1991); White et al., *Gen. Pharmac.*, 22:4, 741-748 (1991). The studies by White et al., suggest that saturated fatty acids have vasodilatory activity and that the medium chain fatty acids are far more potent than either the short chain or the long chain ones. By rank, C10 was the most potent, while the $C_4$ compounds were not particularly vasoactive. The effects of the fatty acids appeared to be independent of the endothelium.

Vasodilation is the dilation of vessels, generally resulting in increased blood flow to a part of the body. A wide variety of vasodilator drugs are known and have been used successfully in the treatment of pathophysiological diseases such as hypertension, angina pectoris, and congestive heart failure, to name a few. These agents may be classified according to their primary mechanism of action. One important group of vasodilators, which includes the nitrates and sodium nitroprusside, exert a direct effect on smooth muscle. Sodium nitroprusside acts to directly relax vascular smooth muscle in both arterioles and veins, while the nitrates, such as nitroglycerin, act principally on the venous bed and pulmonary arteries. Another important group of vasodilatory compounds, which includes captopril, enalapril and lislinopril, appear to exert their activity through the inhibition of enzymatic conversion of angiotensin I to angiotensin II, which is a potent constrictor of arteriolar resistance vessels. Alpha and beta-adrenoreceptor blocking agents and calcium antagonists have also been used successfully as vasodilators.

Despite reports of the development of pharmaceutical agents that lower blood pressure, improve congestive heart failure, or hasten recovery from anginal episodes, none of the vasodilator drugs currently available is ideal. A need continues to exist for medicaments that are useful in the treatment of these disorders, and especially for medicaments that not only exhibit a desirable pharmacological profile, but are also non-toxic, do not induce tachyphylaxis, and are inexpensive to manufacture. A need also exists for vasodilators that have a localized vasodilatory effect which can be used to counteract disorders associated with vasoconstriction in localized or regional vascular beds.

It is an object of the invention to provide short and medium chain monoglycerides capable of stimulating vasodilation in arm-blooded animals that are highly non-toxic and suitable for pharmaceutical formulation and administration.

It is another object to provide vasodilatory compounds that have localized vasodilatory effects.

SUMMARY OF THE INVENTION

These as well as other objects and advantages are met by the present invention, which provides a novel method of effecting vasodilation in a warm-blooded animal in need of such treatment. The method involves administering to a warm-blooded animal an effective amount of a vasodilatory monoglyceride of the formula:

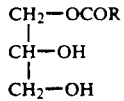

wherein R is a straight or branched chain aliphatic hydrocarbyl substituent of 2–7 carbon atoms, preferably 3–5 carbon atoms, which is saturated or unsaturated, and which is substituted or unsubstituted with one or more substituents that do not interfere with vasodilatory activity. In a preferred embodiment, R is an unsubstituted, straight chain, saturated hydrocarbyl.

These compounds are highly non-toxic and exhibit a potent vasodilatory effect on small vessels of the retinal vasculature and also exhibit a weaker, albeit dose dependent, effect on large arteries.

BRIEF DESCRIPTION OF THE DRAWING

For a more complete understanding of this invention, reference should be made to the drawing, in which.

DETAILED DESCRIPTION OF THE INVENTION

Figure 1:
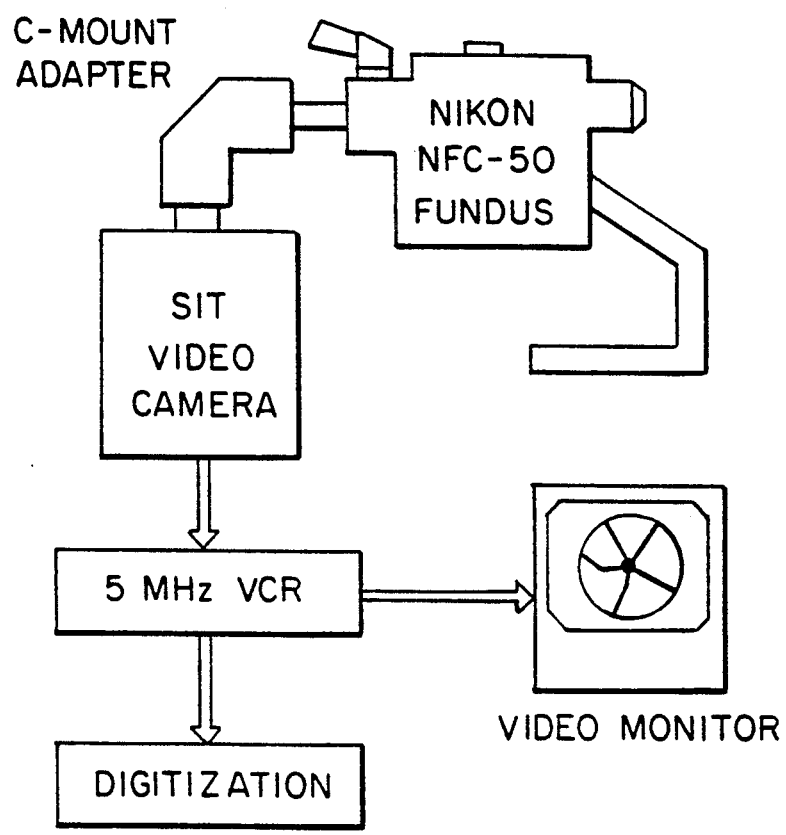
FIG. 1 is a schematic of the video fluorescein angiography system employed in the examples to obtain retinal vessel circulation times and blood flow measurements.

The Compounds Of The Invention And Preparation Thereof

The present invention provides a class of compounds useful in stimulating vasodilation. These compounds can be represented by the following formula 1:

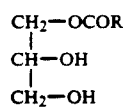

wherein R is a straight or branched chain aliphatic hydrocarbyl radical having from 2–7 carbon atoms, which can be saturated or unsaturated, and which may be substituted by one or more substituents that do not interfere with the vasodilatory activity of the compound. In a preferred embodiment, R is a straight chain aliphatic hydrocarbyl radical containing 3–5 carbon atoms, and most preferably, has 3 carbon atoms.

The group represented by R may be saturated or unsaturated and, if saturated, preferably has less than four pi bonds, preferably three or less, and most preferably two or less. While the embodiments include branched chains, highly branched R groups are not favored, and straight chains are preferred.

Substituents which are preferred are typically those that do not drastically alter the lipophilic character of the compound, and a small, rather than a large number of substituents is preferred. Preferred substituents include halo, in particular chloro, and methoxy.

The compounds of formula 1 of the invention can be prepared conventionally by esterification of glycerol and purification of the monoesterified product. Isolation of the monoester can be done by any standard means, such as chromatographic separation or fractional distillation. Many of the compounds of formula 1 are commercially available; monobutyrin itself, for example, is available from Eastman Kodak.

For purposes of illustration, a protocol for the purification of commercially available monobutyrin to a purity level of greater than 99% is as follows:

Practical grade monobutyrin having a boiling point of 153° C. is subjected to vacuum distillation at about 3 mm Hg over an oil bath held at 160°–162° C. and the distillate obtained at 137°–138° C. is recovered. This fraction is subjected to gas chromatography through a 50 cm × 1.5 cm column containing 30 g of silica gel, and eluted by gradient elution with hexane:ethylacetate varying from 90:10–20:80 v/v, collecting 10 ml fractions. The results of a typical elution are shown in FIG. 5. The first peak eluted from this chromatography, when obtained preparatively, is recrystallized from ether at −70° C. In a typical procedure, this material was shown to be more than 99% pure by GC and TLC, and confirmed by mass spectrometry to be monobutyrin.

Similar purification procedures can be used for commercial or synthetic preparations of alternate embodiment of the compound of formula 1.

The compounds may also be prepared enzymatically in accordance with techniques established in the art. See e.g, Zaks A. and Russel, A. J., *J. of Biotechnology*, Vol. 8, 259–270 (1988); Otero et al, *Applied Biochem. and Biotech.*, 23:237–47 (1990).

Assays Methods

There are a number of different assays that can be used to demonstrate the vasodilatory activity of the compounds useful in the method of the invention. A relatively recent approach to detect vasodilatory activity, especially in smaller vessels, is described in the examples herein. This technique uses a video-based fluorescein angiography (VFA) system (VFA) to investigate retinal circulatory changes in response to vasoactive compounds. Changes in both systemic and retinal circulation can be detected. An added advantage of this technique is that it allows for direct visualization and measurement of vasodilation of the retinal arteries and veins.

To detect vasodilation in the pulmonary and systemic peripheral vascular beds, any of the conventional assays well known to clinicians skilled in this area of technology can be employed, including assays designed to determine the effect of the compound on arterial and venous tone of various medium and large arteries and veins, and hemodynamic assays, such as blood pressure, left and right ventricle fill pressure, and cardiac output measurements.

UTILITY AND ADMINISTRATION

The compounds of the invention are administered to a warm-blooded animal in need of treatment with a vasodilator, in an amount effective to stimulate vasodilation. By the term "warm-blooded animal" is meant all animals that may experience the beneficial effects of the invention. Foremost among such animals are humans, although the invention is not intended to be so limited.

In one application, the compounds of the invention are useful in stimulating vasodilation in the retinal vasculature, to counteract the effect of decreased blood flow and/or increased pressure in the retinal vessels associated with retinal pathophysiological disorders such as ocular arterial occlusion, retinal hypertension, retinal vein thrombosis, and vasoconstriction associated with the middle stages of diabetic retinopathy, in which tissue becomes perfused due to capillary shutdown. For such applications, the compounds are generally applied topically. The compounds of the invention are also expected to be useful in the treatment of glaucoma, a group of diseases characterized by an increase in intraocular pressure which causes pathological changes in the optic disk and typical defects in the field of vision.

Intraocular pressure has heretofore been lowered with tinolol maleate, a non-selective beta-adrenergic receptor blocking agent, supplied in the form of an ophthalmic solution. See, Juan Grunwald, *Investigative Ophthalmology and Visual Science*, 32:1 (January 1991) in which the effects of tinolol on retinal circulation were evaluated. Because of their potent vasodilatory effects in retinal vessels, the compounds of the present invention will, when applied topically in the eye, have the action of reducing normal, as well as elevated intraocular pressure.

The method of the invention may also be useful in the treatment of pathophysiological diseases including acute myocardial infarction, vascular thrombosis, hypertension, pulmonary hypertension, ischemic heart disease, congestive heart failure, and angina pectoris, in which case the compounds may be administered by any means that effect vasodilation and thereby relieve the symptoms of the disease. For example, administration may be by parenteral, subcutaneous, intravenous, intramuscular, intraperitoneal, transdermal, or buccal routes. In view of the freely diffusible nature of these compounds, transdermal administration may be particularly appropriate. Alternatively or concurrently, administration may be by the oral route.

The compounds of the invention may be used alone, or in combination with other of the known vasodilator drugs.

For topical administration as ophthalmic drugs, the compounds of the invention are administered as standard topical formulations, using for example, 0.10 to about 10% solutions or suspensions of the compounds of the invention in a sterile, isotonic, buffered aqueous solution The formulation is delivered in the form of drops in the affected eye, from about 1 to 6, preferably about 2 to 4, times daily. As to dosage, while individual needs may vary, determination of optimal ranges of each compound is well within the skill of the art. A typical dosage contains about 0.10 nanomole to about 5.0 micromoles, preferably about 0.4 micromoles to 4.0 micromoles of the monoglyceride, in a dosage form of about 1 to 4 drops (20 µl/drop).

Alternatively, the active compounds of the invention can be formulated into an ointment containing about 0.10 to 10% of the active ingredient in a suitable base of, for example, white petrolatum, mineral oil and petrolatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules made of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution In addition, stabilizers may be added.

In addition to being provided in a liquid form, for example in a gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch, paste, using for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tables or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, sorbitol, and/or dextran. Optionally, the suspension may also contain stabilizers.

The present invention will be more clearly understood from the following specific examples.

EXAMPLE 1

This example demonstrates that monobutyrin is a potent vasodilator of retinal vessels. In the example, a low light level sensitive video fluoreseein angiography system was employed to investigate retinal circulatory changes in response to histamine, which is a known vasodilator, glycerol, and monobutyrin, using Sprague-Dawley rats.

Instrumentation

A schematic of the video fluorescein angiography (VFA) system used for the real time recordings of retinal fluorescein angiograms is illustrated in FIG. 1. The video camera was interfaced to a standard Nikon NFC-50 retinal fundus camera using a specially built C-mount adaptor. The fundus camera was also fitted with a small pupil adaptor to facilitate imaging of the rat retina. This adaptor consisted of an aperture stop that reduced the size of the standard illumination annulus of the fundus camera. The video camera used was a Dage/MTI silicon intensified target (SIT) camera featuring low light level sensitivity and high resolution (700 video lines at 0.001 foot-candles illumination). The gain of the image intensification stage was set at the same level for all recordings. This gain level, coupled with ⅛ of the maximum fundus camera illumination intensity for excitation, ensured that recorded video levels never saturated during the angiogram. The resulting video images were recorded onto ¾ inch video tape using a high band width (5 Mhz, 500 video line resolution) Panasonic video cassette recorder. These images could then be reviewed on a frame by frame basis for subsequent analysis of the retinal circulatory parameters.

Animal Protocols

VFA recordings were analyzed from a total of 24 male, albino, Sprague-Dawley rats (Taconic, Mass.) weighing between 200 and 500 gm. Of these 24 animals, 16 were given a 10 $\mu$l intravitreal infusion of $10^{-3}$M histamine, 5 were given a 10 $\mu$l intravitreal infusion of a 1:20 dilution (w/w) of monobutyrin (about 99.9% purity, California Biotechnology, Mountain View, Calif.) in phosphate buffered saline and 3 were given an infusion of 10 $\mu$l glycerol. Prior to the experiments, all animals were handed and cared for according to ARVO regulations relating to the use of animal models in research.

On the day prior to VFA measurements, all animals had a heparin lock catheter surgically implanted in the right jugular vein. A 1 inch length of catheter was threaded into the jugular towards the heart and the other end was tunneled subcutaneously and exteriorized at the back of the neck. The rats were anesthetized for this procedure with 0.1 mg/kg sodium amobarbital injected intraperitoneally.

Immediately prior to VFA measurements each rat was again anesthetized with 0.1 mg/kg amobarbital and the pupil of the left eye, contralateral to the jugular vein catheter, was dilated with 1% tropicamide. VFA measurements were made only from the left eye to avoid possible changes in blood flow delivery related to jugular vein catheterization. Retinal circulation times, calculated as described below, were taken for the anesthetized animals before infusion of the active ingredient.

The active ingredient was then infused into the vitreous of the animals. This techniques allows for an investigation of the local effect of the agent, as it is restricted to the eye, and measurements are not complicated by any systemic changes associated with the agent. The intravitreal infusion involved the insertion of a needle just posterior to the limbus of the eye. This was performed under direct visualization making sure that the lens was not punctured and that the needle did not penetrate the retina. The tip of the needle was positioned directly above the optic disk region and a 10 $\mu$l volume of the active agent was slowly infused into the vitreous.

After infusion of the active ingredient, a Hamilton syringe filled with 40 $\mu$l of 10% fluorescein dye was connected to the jugular catheter. The rat was positioned on a platform attached to the chin rest of the fundus camera and a focused image of the retina was obtained while viewing the video monitor. It was necessary to use the plus dioptric correction of the fundus cameral to obtain optimal focus of the retinal vessels. The optic disc region was centered in the field of view.

Figure 2:
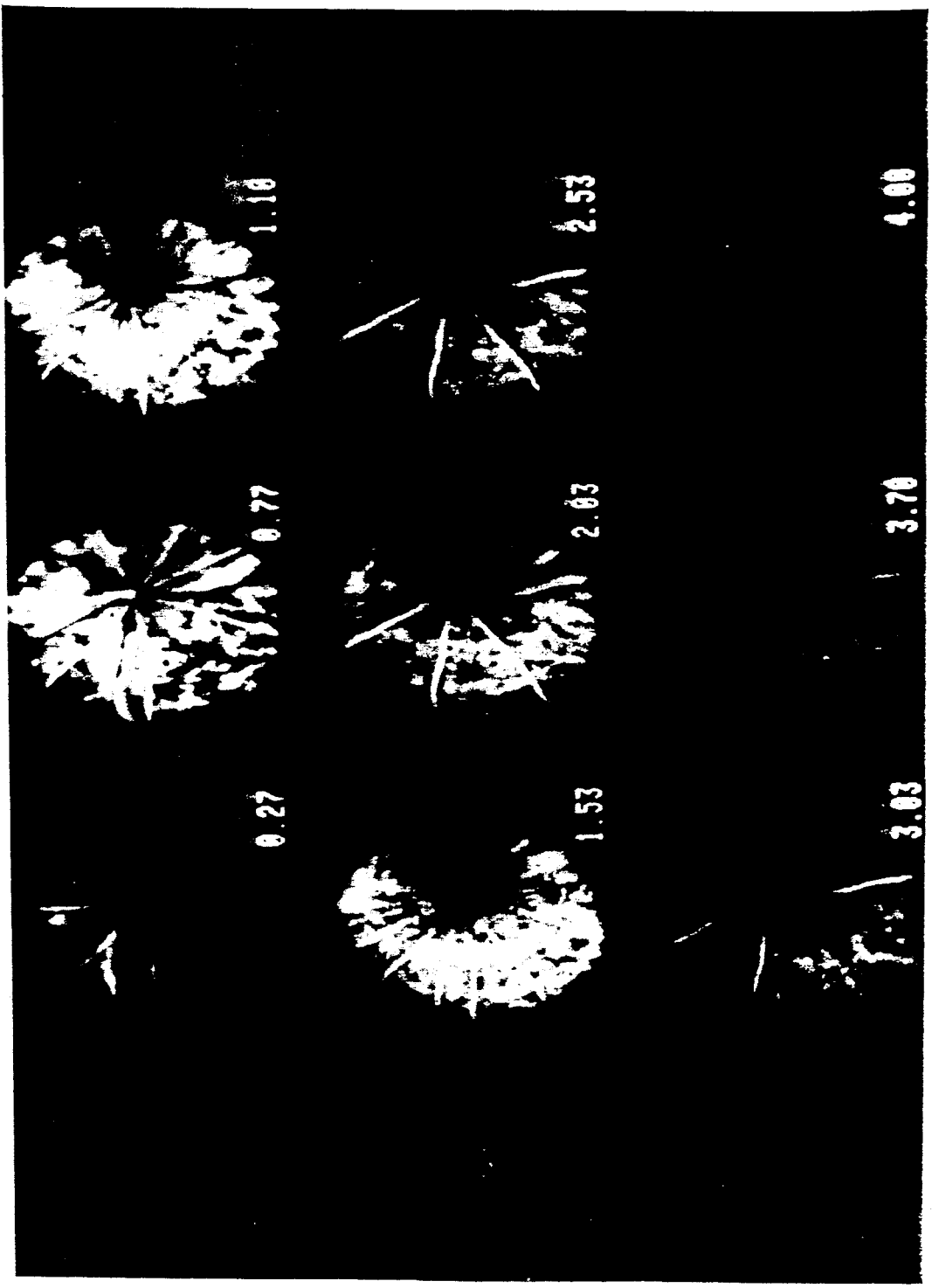
FIG. 2 provides digitized images from a rat VFA recording. Time in seconds (lower right corners) is elapsed time from time of dye appearance in the central retinal artery.

The angiographic sequence was then initiated by inserting the barrier filter in the observation light path and starting the video cassette recorder. A 5 μl bolus of fluorescein dye was rapidly injected (approximately 0.1 seconds) into the jugular vein catheter. The time of injection was marked on the video recording. The fluorescein dye first appeared in the retinal arteries 1 to 2 seconds after the time of injection and cleared from the retinal veins approximately 5 seconds later. In these recordings, the fluorescence of the dye circulating in the retinal vessels is easily visible despite the lack of any screening of background choroidal fluorescence by the retinal pigment epithelium in these albino animals. FIG. 2 illustrates an angiographic sequence obtained from a rat retina.

Six VFA recordings, each following a 5 μl bolus dye injection, were obtained from every rat over a period of 2 to 3 minutes. More recordings were generally not possible as the accumulated background choroidal fluorescence reached a high enough level that the contrast of the dye passage through the retinal vessels became noticeably reduced The total time for this procedure, from time of anesthesia to completion of VFA recordings, was approximately 10 minutes Data Analysis Manual data analyses were performed on these VFA recordings. Prior experience with the system has shown a high, statistically significant correlation between the manual analyses and a computer based image analysis method. The manual method was used as a less costly alternative to the image analysis method. As retinal circulation times calculated using both methods were comparable, the manual analysis method makes this technique more generally accessible to other investigators.

The manual analysis method involved stepping through the recording on a frame by frame basis and determining the retinal artery appearance time (AT) and the retinal arteriovenous passage time (AVP), also referred to as the retinal circulation time. The AT is defined as the time between injection and the first appearance of the dye in the central retinal artery. The AVP time is defined as the time between first dye appearance in the central retinal artery and complete filling of at least 3 veins at the optic disc region. Complete filling is judged to occur when the characteristic venous lamina flow effect disappears and the vein becomes uniformly fluorescent. Image analysis of these recordings confirmed that retinal vessel fluorescence never exceeded the dynamic range of the video camera indicating that the evaluation of vessel filling was not affected by video camera blooming at high fluorescence intensities. In addition, reducing the excitation illumination intensity between one angiogram and another did not significantly alter the calculated AVP times. The choice of complete filling of at least 3 veins in the determination of AVP time was based on the observation that there was heterogeneity in venous filling times. The AVP time thus represents an average retinal circulation time for that particular angiogram. The mean AVP time determined for a particular animal is the AVP times averaged over the 6 separate angiograms.

The computer assisted image analysis of these VFA recordings required that the recorded images be first transferred onto optical disc which facilitated frame by frame digitization of the images. These digitized images were then analyzed densitometrically and the changes in fluorescence intensity, with time, were measured from retinal vessels at a fixed radial distance from the optic disc center. Density measurements were also obtained from 12 other retinal sites adjacent to the arteries and veins to determine average background fluorescence in each image. Further information about the computer assisted image analysis method can be obtained from Dr. Sven Bursell, Beetham Eye Institute, Joslin Diabetes Center, Boston, Mass.

The results of these experiments are set forth in Table 1 below.

TABLE 1

| Animals | Baseline (sec.) | Post Infusion (sec.) | Decrease in AVP (sec.) | % Decrease In AVP |
|---|---|---|---|---|
| HISTAMINE | | | | |
| 1 | 1.31 ± .05 | 1.07 ± .22 | .24 | 18.32 |
| 2 | 1.53 ± .17 | 1.14 ± .09 | .39 | 25.49 |
| 3 | 1.39 ± .02 | 1.24 ± .11 | .15 | 10.79 |
| 4 | 1.62 ± .07 | 1.4 ± .24 | .22 | 13.58 |
| 5 | 1.69 ± .02 | 1.21 ± .14 | .48 | 28.40 |
| 6 | 1.52 ± .16 | 1.17 ± .06 | .35 | 23.03 |
| 7 | 1.52 ± .07 | 1.38 ± .09 | .14 | 9.21 |
| 8 | 1.61 ± .19 | 1.57 ± .16 | .04 | 2.48 |
| 9 | 1.73 ± .09 | 1.32 ± .03 | .41 | 23.70 |
| 10 | 1.43 ± .15 | 1.5 ± .14 | −0.07 | −4.90 |
| 11 | 1.78 ± .02 | 1.38 ± .13 | 0.4 | 22.47 |
| 12 | 1.64 ± .05 | 1.47 ± .11 | .17 | 10.37 |
| 13 | 2.09 ± .18 | 1.58 ± .12 | .51 | 24.40 |
| 14 | 1.88 ± .05 | 1.63 ± .1 | .25 | 13.30 |
| MONOBUTYRIN | | | | |
| 1 | 1.81 ± .06 | 1.08 ± .06 | .73 | 40.33 |
| 2 | 1.43 ± .06 | 1.09 ± .05 | .34 | 23.77 |
| 3 | 1.60 ± .11 | 1.23 ± .11 | .37 | 23.13 |
| 4 | 1.67 ± .07 | 1.25 ± .11 | .42 | 25.15 |
| 5 | 1.39 ± .02 | 1.22 ± .16 | .17 | 12.23 |
| GLYCEROL | | | | |
| 1 | 1.68 ± .16 | 1.60 ± .08 | .08 | 4.76 |
| 2 | 1.77 ± .19 | 1.83 ± .08 | −.06 | −3.39 |
| 3 | 1.55 ± .04 | 1.69 ± .11 | −.14 | −9.03 |

A comparison of retinal circulation times (AVP) before and after histamine infusion showed a significant decrease (p=0.001) in the average retinal circulation time (0.25±18 sec) five minutes after intravitreal infusion. The decrease in retinal circulation time together with an observed vessel dilation indicated a significant blood flow increase in response to histamine, as would be expected for this known vasodilatory agent. AT did not change significantly, suggesting that there were no major effects on the systemic circulation.

The result of infusion with a 1:20 ($4\times10^{-1}$M) dilution of monobutyrin demonstrated a significant (p=0.013) decrease in retinal circulation times (0.40±0.21 sec) compared to preinfusion values. At the same time, there were no changes in the systemic circulation, indicating that the local response in the eye was related solely to the effect of monobutyrin. The negative control experiment performed in three animals using glycerol showed no significant (p=0.60) change in retinal circulation time in response to glycerol, indicating that glycerol itself is not a vasoactive compound.

The decrease in circulation time in response to monobutyrin was almost twice that observed for histamine indicating that monobutyrin is a much more powerful vasodilator.

EXAMPLE 2

This example demonstrates the effect of using lower doses of monobutyrin on blood flow.

These experiments were carried out substantially as described in Example 1, except that the investigation involved the infusion of concentrations ranging from 0.40M to $1\times10^{-9}$M monobutyrin dissolved in phosphate buffered saline (PBS). Concentrations of monobutyrin were coded and masked until completion of the calculations of retinal circulation times. Circulation times were measured before and 10 minutes after infusion with 10 μl of the active ingredient. The results, expressed as the % decrease in AVP or retinal circulation time, are set forth in Table 2 below.

TABLE 2

| Number of Animals | Concentration (M) | % Decrease in AVP | SD |
|---|---|---|---|
| 5 | 0.40 | 24.6 | 10.5 |
| 2 | 0.004 | 31.3 | 11.5 |
| 2 | 0.0004 | 30.4 | 4.7 |
| 3 | $4 \times 10^{-05}$ | 32 | 10.4 |
| 2 | $1 \times 10^{-05}$ | 27.4 | 2 |
| 3 | $4 \times 10^{-06}$ | 24.4 | 11.6 |
| 2 | $1 \times 10^{-06}$ | 21.6 | 11 |
| 2 | $1 \times 10^{-07}$ | 13 | 10.5 |
| 2 | $1 \times 10^{-09}$ | 4.7 | 5 |

Figure 3:
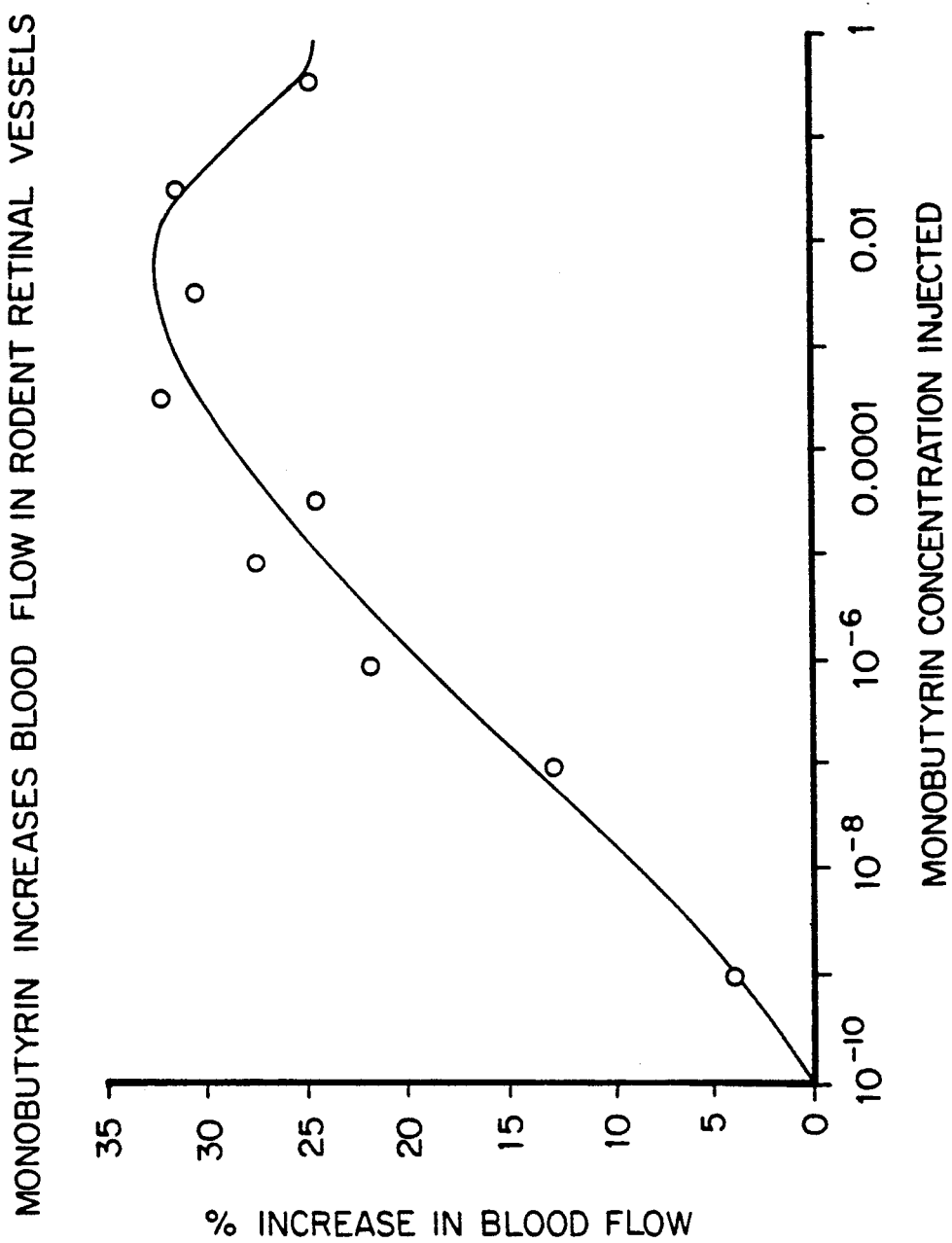
FIG. 3 is the dose response curve obtained for monobutyrin using video fluorescein angiography to assess retinal circulation times 10 minutes after monobutyrin infusion. Each data point represents the average % increase in blood flow for 2–5 animals. The % increase in blood flow was considered directly proportional to the percentage decrease in measured retinal circulation times.

The dose response obtained from the raw data is summarized in FIG. 3. As illustrated in FIG. 3, the greatest response was obtained at a concentration of about $4\times10^{-3}$M monobutyrin, with the EC$_{50}$, i.e., the dosage inducing half maximal response, being about $4\times10^{-6}$M monobutyrin. These results indicate that the concentration of monobutyrin tested had significant effects on retinal circulation times, even at very low values, indicating that the compounds will be useful for topical and systemic application.

EXAMPLE 3

This example investigates the effect on monobutyrin on arterial tone.

Rabbit aortas were obtained immediately after sacrifice of 8-12 week old rabbits. Immediately after removal, the vessels were placed in ice-cold physiologic salt solution (PSS) containing 118.3 mM NaCl, 4.7 mM KCl, 2.5 mM CaCl$_2$, 1.2 mM MgSO$_4$, 1.2 mM KH$_2$PO$_4$, 25.0 mM NaHCO$_3$, 11.1 mM glucose, and 0.026 mM calcium disodium (ethylenedinitrilo)-tetraacetate. The vessels were then cleaned of adventitial tissue and cut into rings of approximately 5 mm lengths. When called for by the protocol, endothelium was removed from a ring by gently rubbing the luminal surface with a watchmaker's forceps.

Vascular rings with intact endothelium were then suspended in organ chambers containing 25 ml of PSS at 37° C. aerated with 95% O$_2$-5% CO$_2$. The rings were connected to force transducers (Grass FT03C, Quincy, Mass.) and changes in isometric force recorded continuously (Grass Polygraph Model 79B) over a period of 90 minutes. The optimal length-tension relationship was determined for each ring by observing the response to $10^{-6}$M norepinephrine after increments in tension of 0.5 gm. The functional integrity of the endothelium was assessed by contracting the vessel with $10^{-6}$M norepinephrine and then observing the response to $3\times10^{-7}$M acetylcholine chloride. Vascular rings that did not relax with acetylcholine chloride were assumed to be denuded o endothelium.

Figure 4:
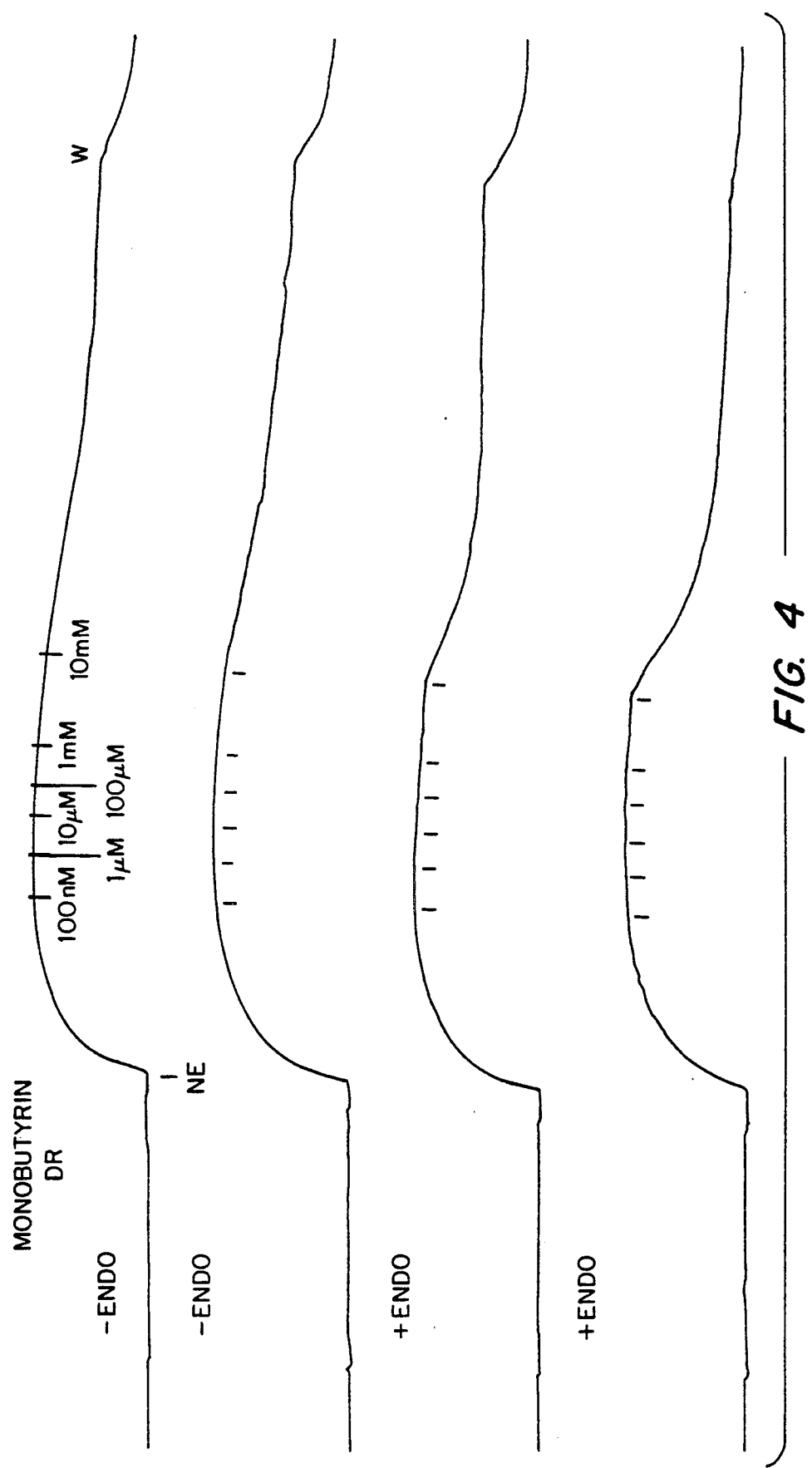
FIG. 4 depicts charts showing the effect of monobutyrin on the contraction of rabbit aorta to norepinephrine. The top two charts show the effect on monobutyrin on vessels removed of the endothelium (Endo-), while the bottom two charts show the effects of the compound on intact vessels. Concentration of monobutyrin ranged from 100 nanomolar to 10 millimolar ($1 \times 10^{-7}$M to $1 \times 10^{-2}$M). The data show that monobutyrin induced a dose-dependent relaxation, although a relatively high concentration of monobutyrin was required to achieve the $EC_{50}$ value, which is about 2mM.

Vascular ring segments with intact endothelium were maximally contracted with a concentration of norepinephrine inducing a halfmaximal response. After a stable contraction had been achieved, the tissue was exposed to increasing concentrations of monobutyrin in log increments. As shown in FIG. 4, progressive relaxation was observed with the apparent EC50 being about 2 mM. These effects were similar for vessels with and without the endothelium. Tachyphylaxis was not observed.

The results indicate that monobutyrin can induce direct relaxation of mammalian vascular arteries that is reversible and not dependent on endothelial mechanisms.

The foregoing examples are illustrative, but not limiting, of the method and compositions of the present invention. Other suitable modifications and adaptations of the variety of conditions and parameters normally encountered in clinical therapy and which are obvious to those skilled in the art are within the spirit and scope of the present invention.

Having described the invention, what is claimed is:

1. A method of effecting vasodilation, comprising:
administering to a warm-blooded animal in need of such treatment, an amount of a vasodilatory monoglyceride of the formula:

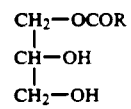

wherein R is a straight chain aliphatic hydrocarbyl substituent of 2-7 carbon atoms which is saturated or unsaturated, and which is substituted or unsubstituted with one or more substituents that do not interfere with vasodilatory activity,
which amount is effective to stimulate vasodilation in the animal.

2. A method according to claim 1 wherein R is an unsubstituted, straight chain, saturated hydrocarbyl.

3. A method according to claim 2, wherein the compound of the formula is monobutyrin.

4. A method according to claim 1 wherein the animal requires vasodilation of retinal vessels in an eye.

5. A method according to claim 4, wherein the compound is administered by placing drops of said compound in a pharmaceutically acceptable formulation in the animal's eye, in an amount of about 0.1 nanomole to about 4.0 micromole of the compound.

6. A method according to claim 1 which includes administering the compound in admixture with a pharmaceutically acceptable excipient.

* * * * *